United States Patent [19]

DonMichael

[11] Patent Number: 4,998,530
[45] Date of Patent: Mar. 12, 1991

[54] RESUSCITATION AID

[76] Inventor: T. Anthony DonMichael, 309 Panorama Dr., Bakersfield, Calif. 93305

[21] Appl. No.: 419,658

[22] Filed: Oct. 11, 1989

Related U.S. Application Data

[63] Continuation-in-part of Ser. No. 202,101, Jun. 1, 1988, abandoned.

[51] Int. Cl.$^5$ ............................................. A61M 16/00
[52] U.S. Cl. ........................... 128/203.11; 128/202.28; 128/207.16
[58] Field of Search ...................... 128/202.28, 202.29, 128/203.11, 207.16

[56] References Cited

U.S. PATENT DOCUMENTS

| | | | |
|---|---|---|---|
| 409,954 | 5/1843 | Martindale et al. | 128/146 |
| 1,142,990 | 6/1915 | Stern . | |
| 2,591,953 | 4/1952 | MacLean | 128/146 |
| 2,887,104 | 5/1959 | Sovinsky et al. | 128/29 |
| 3,229,689 | 1/1966 | Christman | 128/29 |
| 3,252,457 | 5/1966 | Monaco et al. | 128/29 |
| 3,827,433 | 8/1974 | Shannon | 128/145.5 |
| 3,957,046 | 5/1976 | Harris | 128/203.11 |
| 3,974,829 | 8/1976 | Tate, Jr. | 128/146.2 |
| 4,305,387 | 12/1981 | Reist-Kundig et al. | 128/202.28 |
| 4,328,798 | 5/1982 | Isaacson | 128/202.27 |
| 4,449,526 | 5/1984 | Elam | 128/206.21 |
| 4,573,463 | 3/1986 | Hall | 128/205.24 |
| 4,579,114 | 4/1986 | Gray et al. | 128/203.11 |
| 4,697,587 | 10/1987 | Marinkovich | 128/203.11 |
| 4,819,627 | 4/1989 | Connors | 128/203.11 |
| 4,819,628 | 4/1989 | Eisenbert et al. | 128/203.11 |
| 4,858,605 | 8/1989 | Levy | 128/203.11 |

FOREIGN PATENT DOCUMENTS

88/04187 6/1988 World Int. Prop. O. ...... 128/203.11

OTHER PUBLICATIONS

"Infectious Disease", the Newspaper of Cardiology, Aug. 1990, p. 8, Silicon Mask May Reduce AIDS Fear Among CPR-Trained First Responders.

Primary Examiner—Eugene H. Eickholt
Attorney, Agent, or Firm—Spensley Horn Jubas & Lubitz

[57] ABSTRACT

A medical device for enabling a rescuer to administer mouth-to-mouth resuscitation to a victim while maintaining a sanitary barrier between victim and rescuer, composed of: a sheet of a flexible material forming a barrier to micro-organisms, the sheet being dimensioned to completely cover the victim's mouth and having an opening surrounded by a portion of the sheet which is shaped to allow the rescuer's lips to form an air-tight seal with the victim's lips; means secured to the sheet and located to pass around the victim's ears in order to hold the sheet in place so that the opening is located in front of the victim's mouth; a tubular member defining a confined air passage extending through the opening and having a first portion located to be inserted into the victim's mouth when the sheet is in place and a second portion located to be inserted into the mouth of the rescuer; and a one-way valve fastened to the first portion of the tubular member for permitting free passage of air only from the rescuer to the victim.

13 Claims, 2 Drawing Sheets

RESUSCITATION AID

CROSS REFERENCE TO RELATED APPLICATION

This is a continuation-in-part of my copending application Ser. No. 07/202,101, filed on June 1, 1988, abandoned and entitled MASK FOR PERFORMING RESUSCITATION.

BACKGROUND OF THE INVENTION

The present invention relates to resuscitation aids, particularly devices for facilitating mouth-to-mouth resuscitation.

As used herein, mouth-to-mouth resuscitation refers to methods in which air is forced from the lungs of a rescuer into the lungs of a victim of stopped breathing at regular intervals to provide the interchange of air necessary for respiration. If a victim of stopped breathing is to be saved from death, resuscitation must be started promptly after the cessation of breathing. At times, the heart may also have stopped, in which case simultaneous cardiac resuscitation will also be necessary.

Mouth-to-mouth resuscitation, frequently referred to as the "kiss of life", is a technique which is known to a significant portion of the population, particularly since it is not difficult to learn and does not require special equipment.

Unfortunately, the classic mouth-to-mouth technique requires direct contact between rescuer and victim, and many individuals find this aspect of the technique objectionable. Such objections have become even more prevalent because of the fear of transmission of the AIDS virus, given that a victim is often a stranger to a potential rescuer. Because of this fear, even trained paramedic personnel have become reluctant to administer mouth-to-mouth resuscitation.

Many devices have been developed for performing resuscitation in which no mouth-to-mouth contact is required between rescuer and victim. These devices usually involve inserting some type of tube into the airway of a victim. Among these devices are intubation devices, esophageal obturator airways and "bag valve mask" devices.

In order for such devices to be fully effective, they should establish an effective seal over the victim's mouth when air is being breathed into the victim. Many of the known devices are incapable of forming such a seal.

In addition, many known devices are relatively complicated and expensive so that they could not be made widely available for general use. Since resuscitation must be started within minutes after a stoppage of breathing, devices which cannot be made widely available and/or which can only be used by a small number of highly trained personnel are of little practical value.

Thus, mouth-to-mouth resuscitation remains the technique which offers the greatest hope of assistance to a victim of stopped breathing. Because the lips and associated facial muscles of such a victim are flaccid, virtually no known resuscitation aid can produce a perfect seal with the victim's lips. A nearly perfect seal can be created, however, if the rescuer purses his lips and then covers the victim's mouth. Such perfect seal is due in large measure to the ability of the rescuer to close his lips over the mouth area of the victim and thus perfectly conform to that area.

Pending U.S. application Ser. No. 202,101, filed on June 1, 1988, describes a disposable device which enables such a seal to be created while preventing the transmission of air and other fluids from the victim to the rescuer.

SUMMARY OF THE INVENTION

It is a primary object of the present invention to provide a number of substantial improvements in the mask disclosed in the earlier application.

A more specific object of the invention is to provide an improved mask which can be more reliably positioned to establish an airway for a victim.

Another specific object of the invention is to provide an improved mask which is inexpensive to manufacture and highly portable, so that the mask can be easily carried by anyone and, because of its low cost, can be disposed of after use.

The above and other objects are achieved, according to the present invention, by a medical device for enabling a rescuer to administer mouth-to-mouth resuscitation to a victim while maintaining a sanitary barrier between victim and rescuer, comprising:

a sheet of a flexible material forming a barrier to micro-organisms, the sheet being dimensioned to completely cover the victim's mouth, the sheet having an opening and a shaped portion which surrounds the opening and is shaped to allow the rescuer's lips to form an air-tight seal with the victim's lips when the rescuer is blowing air into the victim's mouth, the sheet, including the shaped portion, being formed to permit the victim to exhale without obstruction when the rescuer's lips are withdrawn from the sheet;

a tubular member defining a confined air passage extending through the opening and having a first portion located to be inserted into the victim's mouth and over the victim's tongue when the sheet is in place and a second portion located to be inserted into the mouth of the rescuer; and means defining a one-way valve fastened to the first portion of the tubular member for permitting free passage of air only from the rescuer to the victim.

DESCRIPTION OF THE PREFERRED EMBODIMENTS

Figure 1:
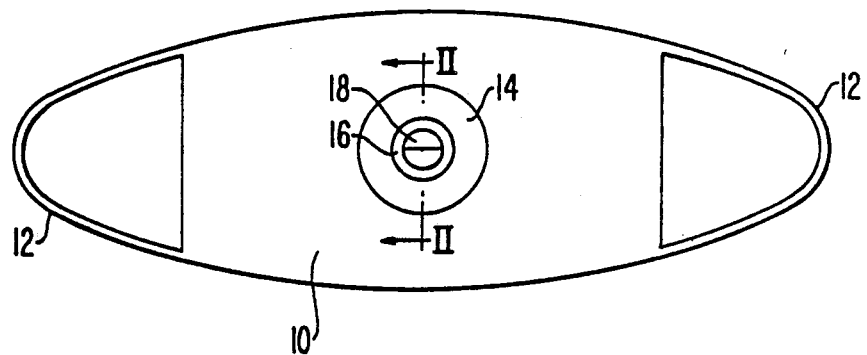
FIG. 1 is an elevational view of a preferred embodiment of a mask according to the present invention.
Figure 2:
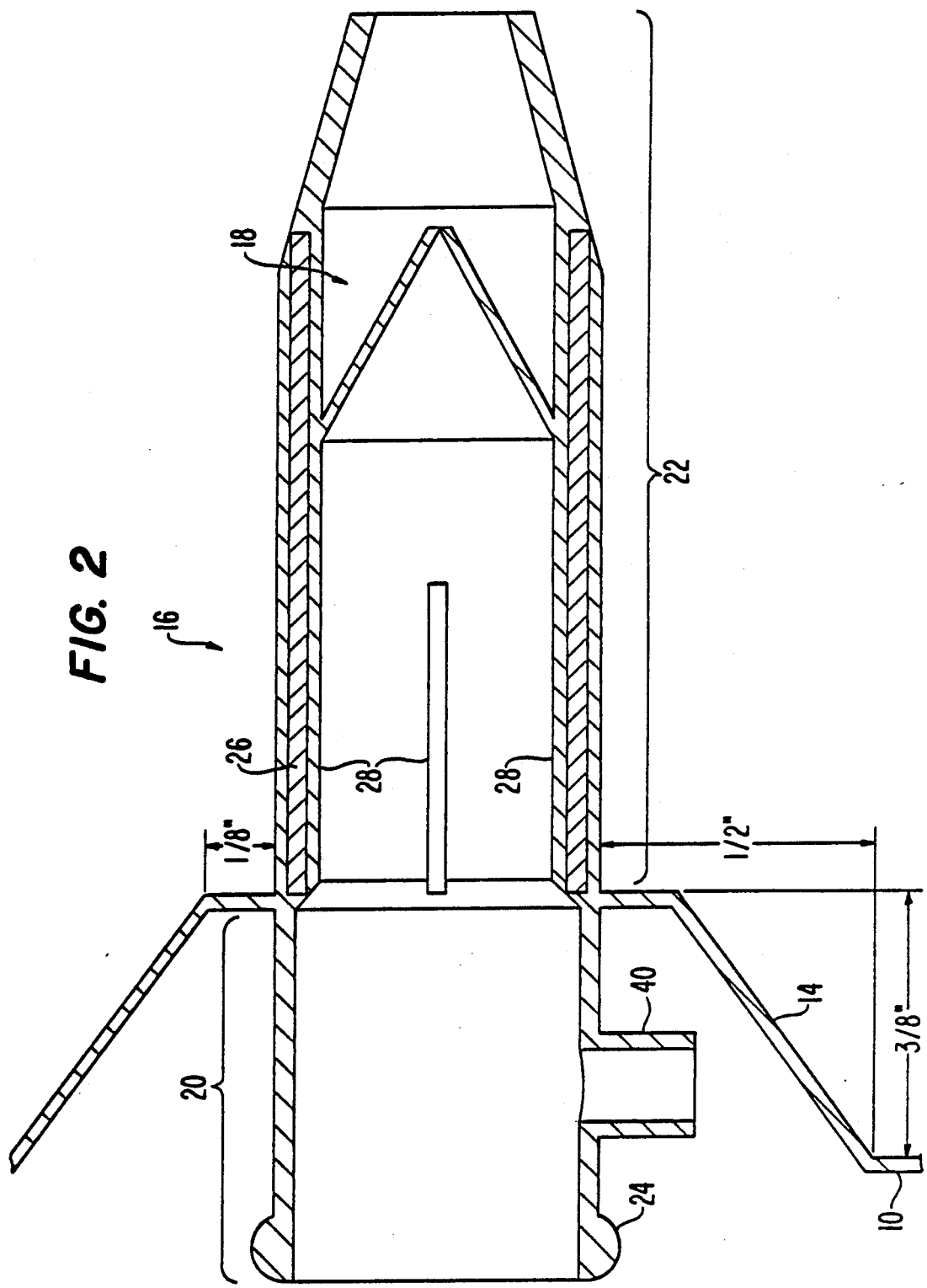
FIG. 2 is a cross-sectional view of the airway portion of the mask of FIG. 1, taken along the line II—II of FIG. 1.

The mask shown in FIGS. 1 and 2 is essentially a one-piece molded plastic article preferably made of a flexible, transparent or semitransparent plastic or a clear silicone rubber, the latter material presently being preferred. As shown in FIG. 1, the mask is composed of a generally elliptical cover sheet 10 provided at its ends with straps 12 which are preferably molded integrally with sheet 10. Essentially at the center of sheet 10 there is provided a frustoconical lip portion 14 which is connected to a tube 16 provided at one end with a one-way valve 18 and constituting an airway via which air can be transferred from the rescuer to the victim. In addition, the mask is sized to cover the victim's nostrils. Even though the mask covers the victim's nostrils, it is still necessary for the rescuer to pinch the victim's nose when exhaling into the victim, in accordance with standard CPR practice. However, if the victim's nostrils are covered by the mask, the mask will serve as a barrier protecting the rescuer from contamination in the event the victim experiences vomiting through the nose during resuscitation.

As shown in FIG. 2, tube 16 and its associated valve 18 are preferably molded integrally with sheet 10 and lip portion 14.

According to one advantageous feature of the present invention, the mask is to be secured in place on the victim, with straps 12 placed around the victim's ears, rather than being worn by the rescuer. Therefore, once tube 16 has been inserted into the victim's mouth and properly positioned, it will remain in place even if the rescuer should remove his mouth from tube 16.

Referring now more specifically to FIG. 2, tube 16 includes a first portion 20 located at the side of the mask which will face the rescuer and a second portion 22 which will be inserted into the victim's mouth at the time the mask is placed on the victim. A bead 24 around the free end of portion 20 assists retention of portion 20 in the rescuer's mouth. Portion 22 is given a length sufficient to assure that it will rest upon the victim's tongue without extending so far as to contact the victim's throat, which would cause gagging, and possible vomiting. It is presently contemplated that this will be achieved if portion 22 has a length of the order of 2 to 2¼ inches. Preferably, portion 20 has a length of the order of ¾ to 1 inch.

Lip portion 14 constitutes a significant component of the mask in that its configuration assures that the rescuer's lips can use lip portion 14 to form a "kiss" which creates an air-tight seal with the victim's lips during the times when the rescuer is blowing air into the victim's mouth, even though the victim's lips are usually flaccid. In effect, the form of lip portion 14 has been painstakingly developed to allow the rescuer's lips to establish an effective seal which makes possible efficient delivery of air to the victim's lungs to an extent comparable to that which can be achieved by direct contact mouth-to-mouth resuscitation.

Moreover, the function of lip portion 14 is such that when the rescuer's mouth is withdrawn, the victim can readily exhale around portion 14.

The preferred relevant dimensions for lip portion 14 are shown in FIG. 2 for a mask made of 50 Durometer clear silicone rubber with lip portion 14 having a thickness of the order of 1/16 inch. The dimensions shown in FIG. 2 have been found to be suitable for individuals having a wide range of sizes. Bead 24 can assist the rescuer to place his mouth in the correct position relative to lip portion 14.

As can be seen from both FIGS. 1 and 2, valve 18 is preferably of the type having two flat sides which meet at a closing line, the valve thus being of the type which is referred to a "fish mouth" valve. When a valve of this configuration is made of the type of material described above, one effective example being as described above (50 Durometer clear silicone rubber, with a wall thickness of the order of 1/16 inch), it has been found that this valve will open easily to permit the passage of air in the direction from the rescuer to the victim, but will form a tight seal with respect to the transmission of air in the opposite direction. In fact, tests have shown that this valve is impermeable to the transmission of the AIDS virus in the direction from the victim to the rescuer.

At the free end of portion 22, tube 16 extends beyond valve 18 to provide a protective enclosure which will reduce the possibility that the victim's tongue can assume a position to block valve 18 or to interfere with its function.

Embedded within the region of portion 22 between lip portion 14 and valve 18 is a tube 26 which is relatively rigid, and which may be constituted, for example, by an acrylic or polycarbonate plastic having a thickness of the order of 1/16 inch. Tube 26 is located to be interposed between the teeth of a victim when the mask is in place and thus serves to prevent the victim from involuntarily closing the airway or biting through tube 16 and from closing valve 18 with his tongue.

Tube 26 may be molded in place in the molded silicone rubber mask by being placed on a core having four radial projections which support the inner surface of tube 26, silicone rubber then being molded around tube 26 as the mask is being produced. When the resulting mask is removed from the mold, the radial projections of the core will leave slots 28, as shown in FIG. 2. Between slots 28, silicone rubber adheres to the inner surface of tube 26.

According to a particularly advantageous embodiment of the tube 16 shown in FIG. 2, this tube has an interior diameter of the order of 0.6 to 0.7 inch and a wall thickness of the order of 0.04 to 0.1 inch, although other dimensions may prove suitable.

Generally, tube 16 has a circular cross section and it is particularly preferred that at least portion 20 have this cross section so that the rescuer can grip portion 20 in his mouth with his head having any orientation relative to that of the victim.

Figure 3:
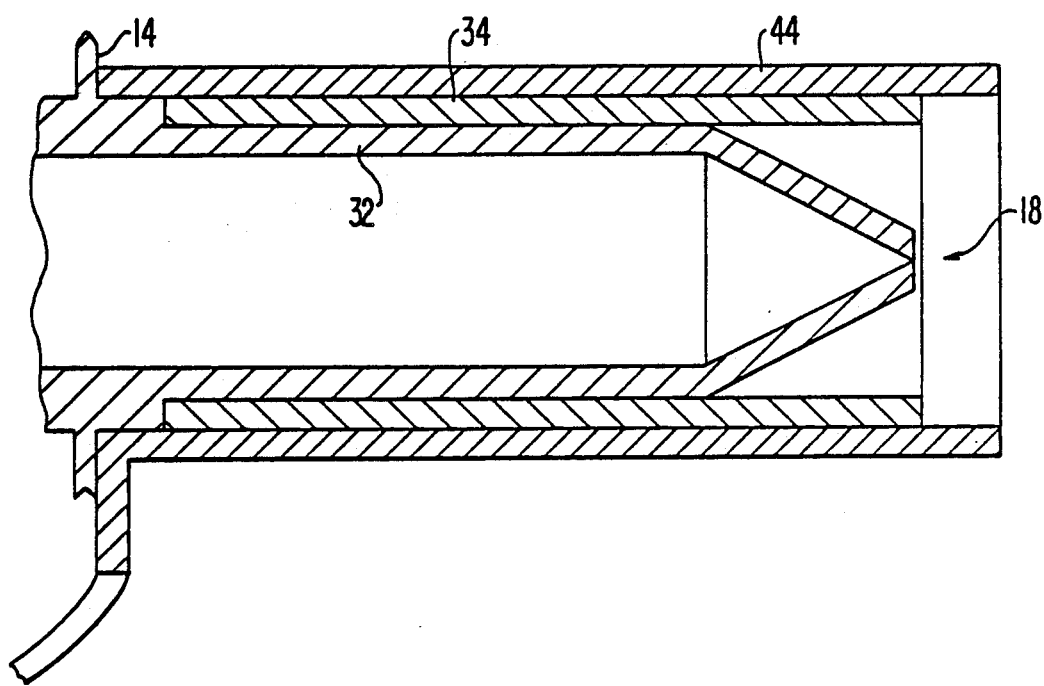
FIG. 3 is a view similar to that of FIG. 2 of a second embodiment of an airway according to the present invention.

A second embodiment of a tube according to the present invention is illustrated in FIG. 3. This tube is structurally simpler than that of FIG. 2 and is composed of a molded body 32 of soft rubber having valve 18 at its distal end. Tube 32 is additionally provided in the vicinity of lip portion 14, with an annular shoulder 33 and carries a rigid plastic tube 34 which is positioned against shoulder 33. Tube 34 may be made of the same material as tube 26 of FIG. 2 and performs essentially the same function. In addition, tube 34 extends over valve 18 to prevent the victim's tongue from interfering with the operation of valve 18. An embodiment employing the tube shown in FIG. 3 is otherwise identical to that shown in FIG. 2 and includes, in particular, a portion 22 which is to fit into the rescuer's mouth.

As noted earlier herein, the device is placed into use by inserting portion 22 into the victim's mouth so that the distal end of tube 16 or 32 lies upon the victim's tongue.

In the embodiments illustrated in FIGS. 2 and 3, valve 18 is protected from interference by the victim's tongue. However, if such protection is not provided, it is preferred that valve 18 be oriented relative to sheet 10 so that one of the flat, inclined surfaces of valve 18 will rest upon the victim's tongue and will act in the manner of a spatula to depress the tongue when air is being exhaled by the rescuer.

If, during a resuscitation procedure, the victim should experience vomiting, this can be dealt with by removing one of the straps 12 and pulling tube 16 out of the victim's mouth. Since the other strap 12 remains in position, the mask can be easily reinserted after the vomiting episode has terminated.

One feature of a mask according to the present invention is that it does not include any parts which obturate the victim's nose or which must be fit over the victim's chin, so that installation of the mask is simplified.

Embodiments of the invention could also be constructed to include an opening for connection of an auxiliary air supply device and/or to include electrodes via which impulses could be supplied to the victim's tongue and/or lips to perform a cardiac pacing or defibrillation function.

Thus, as shown in FIG. 2, tube portion 20 may be optionally provided with a nipple 40 for connection to an auxiliary air or oxygen supply.

As shown in FIG. 3, the mask may be packaged with a cylindrical metal electrode 44 connected to a wire for use, together with a second electrode, to effect defibrillation, or cardiac pacing. Electrode 44 may be open or closed at its distal end and can be used while mounted on tube 34 or by itself. When electrode 44 is open at its distal end, as shown in FIG. 3, and is installed on tube 34, defibrillation or pacing can be performed simultaneously with resuscitation. The other electrode may be connected to any suitable location on the victim's body.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A medical device for enabling a rescuer to administer mouth-to-mouth resuscitation to a victim while maintaining a sanitary barrier between victim and rescuer, comprising:
   a sheet of a flexible material forming a barrier to micro-organisms, said sheet being dimensioned to completely cover the victim's mouth, said sheet having an opening and a shaped portion of circular form which surrounds said opening and is shaped to allow the rescuer's lips to form an air-tight seal with the victim's lips when the rescuer is blowing air into the victim's mouth, said sheet, including said shaped portion, being formed to permit the victim to exhale without obstruction when the rescuer's lips are withdrawn from said sheet;
   a tubular member defining a confined air passage extending through said opening and having a first portion located to be inserted into the victim's mouth and over the victim's tongue when said sheet is in place and a second portion located to be inserted into the mouth of the rescuer; and
   means defining a one-way valve fastened to said first portion of said tubular member for permitting free passage of air only from the rescuer to the victim.

2. A device as defined in claim 1 further comprising means surrounding said valve and serving as a barrier between said valve and a victim's tongue when said first portion of said tubular member is inserted into the mouth of the victim for preventing the victim's tongue from obstructing said valve.

3. A device as defined in claim 1 wherein said shaped portion of said sheet which surrounds said opening comprises a frustoconical portion surrounding said tubular member to a form a seal with the victim's lips.

4. A device as defined in claim 3 wherein said sheet, said tubular member and said valve are constituted by a one-piece molded member.

5. A device as defined in claim 4 wherein said molded member is of a silicone rubber.

6. A device as defined in claim 1 further comprising a second tubular member of a rigid material held in place relative to said first-recited tubular member to surround the air passage, said second tubular member serving as a bite block to prevent the victim from closing the air passage.

7. A device as defined in claim 1 wherein said first portion of said tubular member is of a length to cause said valve to be located above the tongue of the victim when said first portion is inserted into the victim's mouth and to not induce vomiting by the victim.

8. A device as defined in claim 1 wherein said means defining a one-way valve are constituted by two planar members which contact one another along a line perpendicular to the air passage when said valve is closed, said planar members being moveable away from one another when the air pressure in said air passage is higher than that in the region exterior to and adjacent said valve.

9. A device as defined in claim 1 wherein said sheet, said tubular member and said one-way valve are constituted by a one-piece molded member.

10. A device as defined in claim 9 wherein said molded member is made of a silicone rubber.

11. A device as defined in claim 10 wherein said valve is made of a 50 Durometer silicone rubber.

12. A device as defined in claim 1 further comprising attachment means attached to said sheet for securing said device in place on the victim.

13. A device as defined in claim 1 wherein said sheet is dimensioned to cover the victim's nostrils.

* * * * *